US00PP30357P2

(12) United States Plant Patent
Arts

(10) Patent No.: US PP30,357 P2
(45) Date of Patent: Apr. 9, 2019

(54) ***HYDRANGEA* PLANT NAMED 'H217901'**

(50) Latin Name: *Hydrangea macrophylla*
Varietal Denomination: H217901

(71) Applicant: HYDRANGEA BREEDERS ASSOCIATION B.V., De Kwakel (NL)

(72) Inventor: Niels Arts, Aalsmeer (NL)

(73) Assignee: Hydrangea Breeders Association B.V., De Kwakel (NL)

( * ) Notice: Subject to any disclaimer, the term of this patent is extended or adjusted under 35 U.S.C. 154(b) by 0 days.

(21) Appl. No.: 15/932,555

(22) Filed: Mar. 13, 2018

(51) Int. Cl.
*A01H 5/02* (2018.01)

(52) U.S. Cl.
USPC ..... Plt./250
CPC ..... *A01H 5/02* (2013.01)

(58) Field of Classification Search
USPC ..... Plt./250
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Hydrangea* plant named 'H217901', characterized by its compact, upright and rounded plant habit; vigorous growth habit and moderate growth rate; freely branching habit with strong, thick and sturdy stems; early, freely and uniformly flowering habit; mophead-type inflorescences with numerous double-type sterile flowers that are light red purple in color; and good postproduction longevity.

4 Drawing Sheets

Botanical designation: *Hydrangea macrophylla.*
Cultivar denomination: 'H217901'.

CROSS-REFERENCED TO CLOSELY-RELATED APPLICATIONS

Title: *Hydrangea* Plant Named 'H217902'
Applicant: Niels Arts
Filed: Concurrently Ser. No. 15/932,554 with this application

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'H217901'.

The new *Hydrangea* plant is a product of a planned breeding program conducted by the Inventor in De Kwakel, The Netherlands and Glandorf, Germany. The objective of the breeding program was to create new compact and freely-branching *Hydrangea* plants with strong sturdy stems, large inflorescences with numerous double-type sterile flowers, attractive sterile flower color and good postproduction longevity.

The new *Hydrangea* plant originated from a cross-pollination made by the Inventor in March, 2012 in De Kwakel, The Netherlands, of a proprietary selection of *Hydrangea macrophylla* identified as code number 10-0167-050, not patented, as the female, or seed, parent with a proprietary selection of *Hydrangea macrophylla* identified as code number 10-0167-040, not patented, as the male, or pollen, parent. The new *Hydrangea* plant was discovered and selected by the Inventor as a single flowering plant from within the progeny of the stated cross-pollination in a controlled greenhouse environment in Glandorf, Germany in March, 2013.

Asexual reproduction of the new *Hydrangea* plant by vegetative tip cuttings in a controlled environment in De Kwakel, The Netherlands since April, 2014 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'H217901'. These characteristics in combination distinguish 'H217901' as a new and distinct *Hydrangea* plant:

1. Compact, upright and rounded plant habit.
2. Vigorous growth habit and moderate growth rate.
3. Freely branching habit with strong, thick and sturdy stems.
4. Early, freely and uniformly flowering habit.
5. Mophead-type inflorescences with numerous double-type sterile flowers that are light red purple in color.
6. Good postproduction longevity.

Plants of the new *Hydrangea* can be compared to plants of the female and male parent selections. Plants of the new *Hydrangea* differ primarily from plants of the female and male parent selections in sterile flower form as sterile flowers of plants of the new *Hydrangea* are double-types with several whorls of sepals whereas sterile flowers of plants of the female and male parent selections are single-types with a single whorl of sepals.

Plants of the new *Hydrangea* can be compared to plants of the *Hydrangea macrophylla* 'H217902', disclosed in a U.S. Plant patent application Ser. No. 15/932,554 filed concurrently. In side-by-side comparisons, plants of the new *Hydrangea* differ primarily from plants of 'H217902' in the following characteristics:

1. Plants of the new *Hydrangea* are slightly narrower than plants of 'H217902'.
2. Inflorescences of plants of the new *Hydrangea* are slightly narrower with smaller sterile flowers than plants of 'H217902'.
3. Sterile flower sepals of plants of the new *Hydrangea* are ovate in shape whereas sterile flower sepals of plants of 'H217902' are elliptical in shape.
4. Plants of the new *Hydrangea* and 'H217902' differ in reaction to aluminum sulfate treatment as sterile flower sepals of plants of the new *Hydrangea* treated with aluminum sulfate become light violet blue in color whereas sterile flower sepals of plants of 'H217902' treated with aluminum sulfate become light blue in color.

Plants of the new *Hydrangea* can also be compared to plants of the *Hydrangea macrophylla* 'H216906', disclosed in U.S. Plant patent application Ser. No. 15/731,672. In side-by-side comparisons, plants of the new *Hydrangea* differ primarily from plants of 'H216906' in the following characteristics:

1. Plants of the new *Hydrangea* have shorter inflorescences than plants of 'H216906'.
2. Sterile flowers of plants of the new *Hydrangea* are smaller and more rounded than sterile flowers of plants of 'H216906'.
3. Plants of the new *Hydrangea* have lighter red purple-colored sterile flower sepals than plants of 'H216906'.
4. Plants of the new *Hydrangea* and 'H216906' differ in reaction to aluminum sulfate treatment as sterile flower sepals of plants of the new *Hydrangea* treated with aluminum sulfate become light violet blue in color whereas sterile flower sepals of plants of 'H216906' treated with aluminum sulfate become light purple in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'H217901'.

The photograph on the second sheet is a top perspective view of a typical flowering plant of 'H217901'.

The photograph on the third sheet is a close-up view of a typical flowering plant of 'H217901'.

The photograph on the fourth sheet is a close-up view of a typical inflorescence of a plant of 'H217901' that has been "blued", that is, treated with aluminum sulfate.

DETAILED BOTANICAL DESCRIPTION

Plants used in the aforementioned photographs and in the following description were grown during the late spring and early summer in 13-cm containers in a glass-covered greenhouse in De Kwakel, The Netherlands and under cultural practices typical of commercial *Hydrangea* production. During the production of the plants, day and night temperatures averaged 17° C. Plants of the new *Hydrangea* were one year old when the photographs and description were taken. Plants of the new *Hydrangea* can be successfully treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'H217901'.

Parentage:

*Female, or seed, parent.*—Proprietary selection of *Hydrangea macrophylla* identified as code number 10-0167-050, not patented.

*Male, or pollen, parent.*—Proprietary selection of *Hydrangea macrophylla* identified as code number 10-0167-040, not patented.

Propagation:

*Type cutting.*—By vegetative tip cuttings.

*Time to initiate roots, summer.*—About two weeks at temperatures about 23° C.

*Time to initiate roots, winter.*—About 18 days at temperatures about 20° C.

*Time to produce a rooted young plant, summer.*—About four weeks at temperatures about 23° C.

*Time to produce a rooted young plant, winter.*—About five weeks at temperatures about 20° C.

*Root description.*—Thick; typically whitish brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Compact, upright and rounded plant habit; strong and sturdy stems; moderate growth rate and vigorous growth habit.

*Plant height.*—About 25 cm to 30 cm.

*Plant diameter or area of spread.*—About 40 cm to 50 cm.

Lateral branch description:

*Branching habit.*—Freely branching habit; when pinched, about six to eight lateral branches develop per plant.

*Length.*—About 20 cm to 25 cm.

*Diameter.*—About 4 mm to 5 mm.

*Internode length.*—About 3 cm to 5 cm.

*Texture.*—Smooth, glabrous; fully developed, woody.

*Aspect.*—Upright to about 20° from vertical.

*Strength.*—Strong, sturdy.

*Color.*—When developing: Close to 144C; at internodes, close to 187B; lenticels, close to 187A. Developed: Close to 144B; at the internodes, close to 187B; when woody, close to 177C; lenticels, close to 187A.

Leaf description:

*Arrangement.*—Opposite, simple.

*Length.*—About 8 cm.

*Width.*—About 6 cm to 7 cm.

*Shape.*—Ovate.

*Apex.*—Acute.

*Base.*—Obtuse.

*Margin.*—Serrulate.

*Texture, upper surface.*—Smooth to rugose, glabrous.

*Texture, lower surface.*—Rugose, glabrous.

*Venation pattern.*—Pinnate.

*Color*.—Developing and fully developed leaves, upper surface: Close to 137B; venation, close to 145B. Developing and fully developed leaves, lower surface: Close to 137D; venation, close to 145D.

*Petioles*.—Length: About 2 cm to 2.5 cm. Diameter: About 3 mm to 4 mm. Texture, upper and lower surfaces: Smooth, glabrous. Color, upper and lower surfaces: Close to 145B.

Flower description:

*Flower type and habit*.—Double-type sterile flowers arranged on mophead-type terminal panicles; panicles globular and slightly flattened in shape; flowers face upright to outwardly depending on their position in the inflorescence; no fertile flowers have been observed on plants of the new *Hydrangea* to date.

*Fragrance*.—None detected.

*Natural flowering season*.—Early flowering habit, plants begin flowering about 10 to 15 months after planting; flowering begins in the early summer and is continuous throughout the summer in Northern Europe.

*Flower longevity*.—Sterile flowers last about four months on the plant, sterile flowers persistent.

*Quantity of flowers*.—Freely flowering habit; about 120 to 160 sterile flowers per panicle; to date, no fertile flowers have been observed on plants of the new *Hydrangea*.

*Panicle height*.—About 7 cm to 8 cm.

*Panicle diameter*.—About 10 cm to 15 cm.

*Sterile flower buds*.—Length: About 3 mm. Diameter: About 3 mm. Shape: Rounded. Color: Close to 144B.

*Sterile flower diameter*.—About 2.5 cm by 3.5 cm.

*Sterile flower depth* (*height*).—About 5 mm.

*Petals, sterile flowers*.—Petal development has not been observed on plants of the new *Hydrangea* to date.

*Sepals, sterile flowers*.—Quantity and arrangement: About 13 in about three whorls. Length, outer whorl: About 1 cm to 1.5 cm. Width, outer whorl: About 1.5 cm. Length, inner whorls: About 0.5 cm to 1 cm. Width, inner whorls: About 0.5 cm. Shape: Ovate. Apex: Obtuse. Base: Obtuse. Margin: Entire. Texture, upper and lower surfaces: Smooth, glabrous. Color: When opening, upper and lower surfaces: Close to 145C. Fully opened, upper surface: Close to 73B; when "blued", close to 91B to 91C; colors do not change with development. Fully opened, lower surface: Close to 65B; when "blued", close to 91B to 91C; colors do not change with development.

*Pedicels, sterile flowers*.—Length: About 2 cm to 3 cm. Diameter: About 2 mm to 3 mm. Strength: Strong. Aspect: Erect to about 45° from vertical. Texture: Smooth, glabrous. Color: Close to 65B.

*Reproductive organs*.—To date, reproductive organ development has not been observed on sterile flowers of plants of the new *Hydrangea*; all reproductive organs are "transformed" into inner whorls of sepals.

*Fruits and seeds*.—Fruit and seed development has not been observed on plants of the new *Hydrangea* to date.

Pathogen & pest resistance: To date, under commercial production conditions, plants of the new *Hydrangea* have not been observed to be resistant to pathogens and pests common to *Hydrangea* plants.

Temperature tolerance: Plants of the new *Hydrangea* have been shown to be tolerant to temperatures ranging from about 3° C. to about 38° C.

It is claimed:

1. A new and distinct *Hydrangea* plant named 'H217901' as illustrated and described.

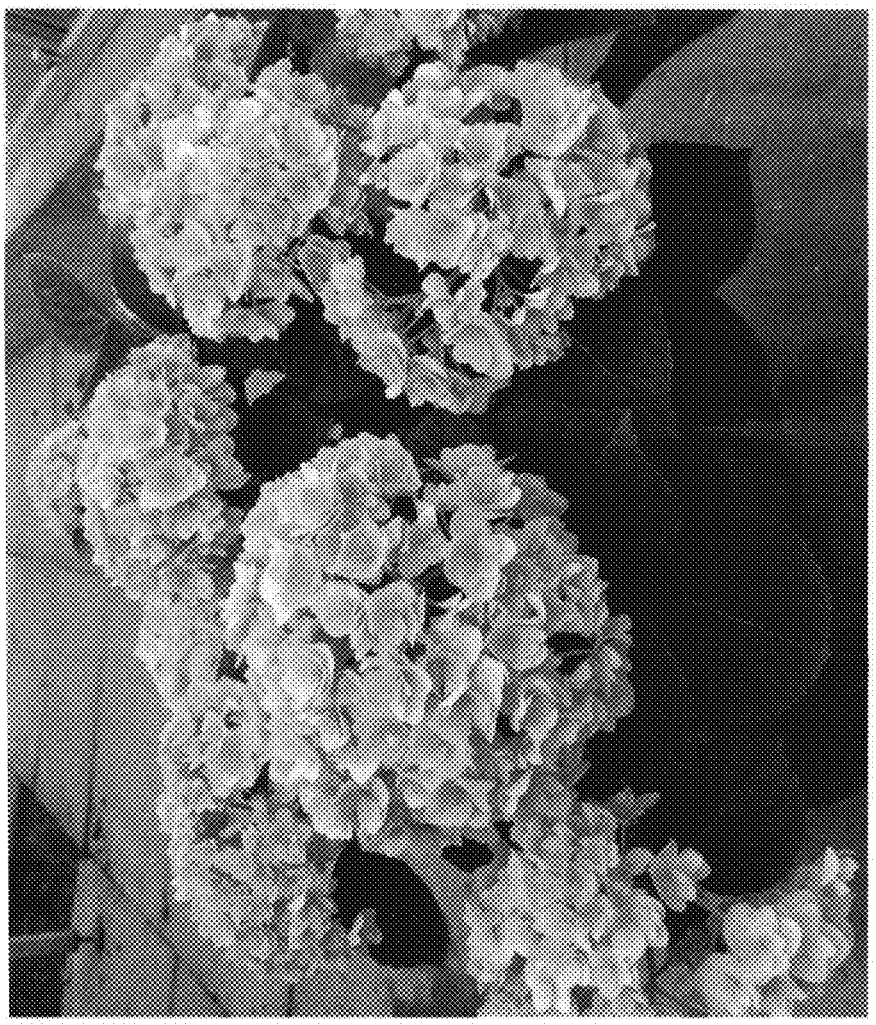

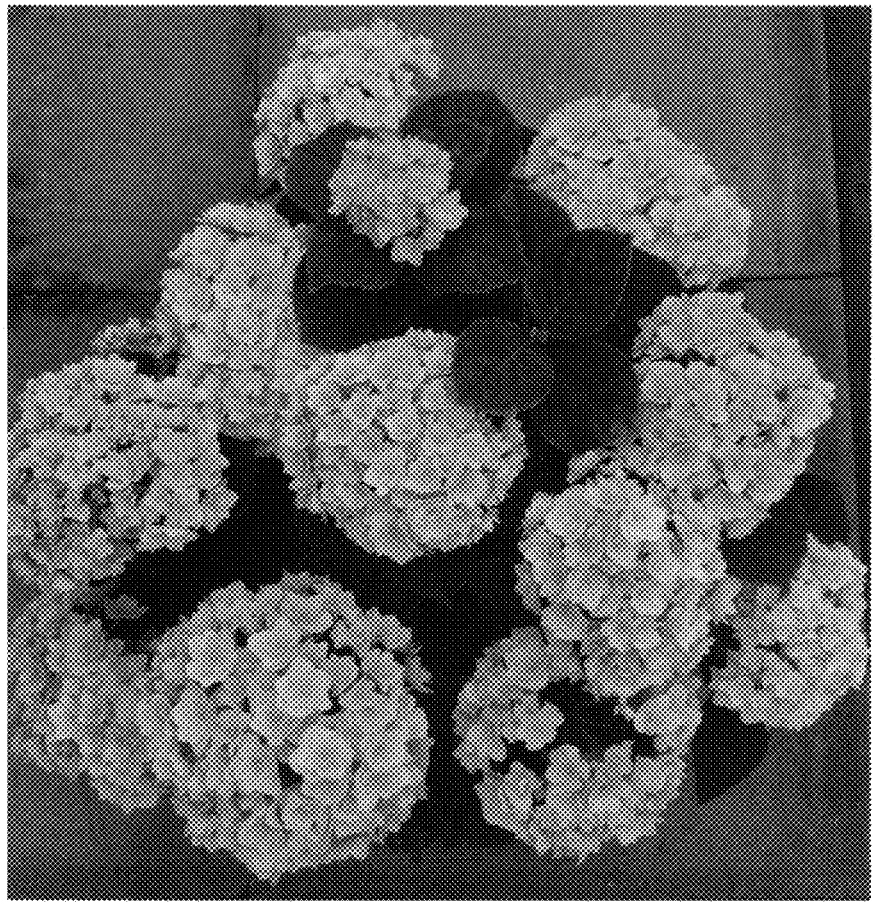

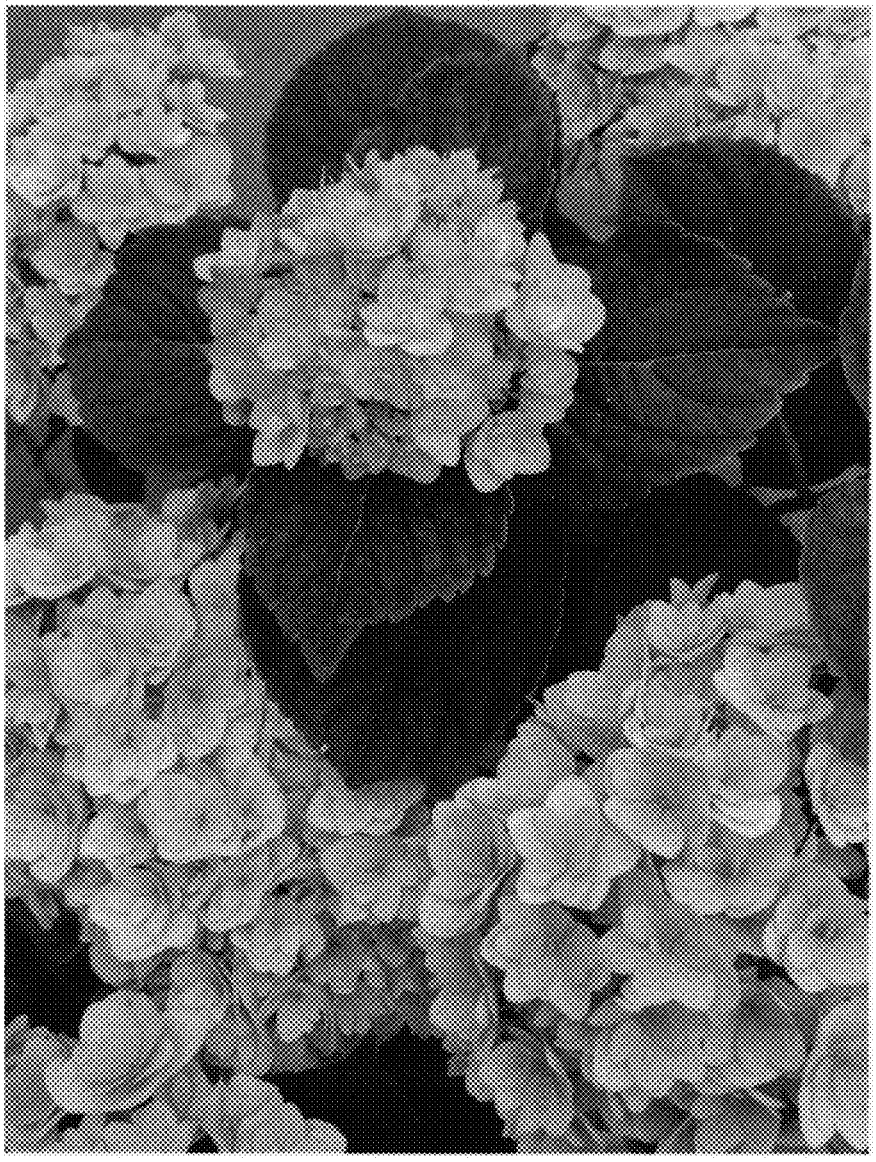

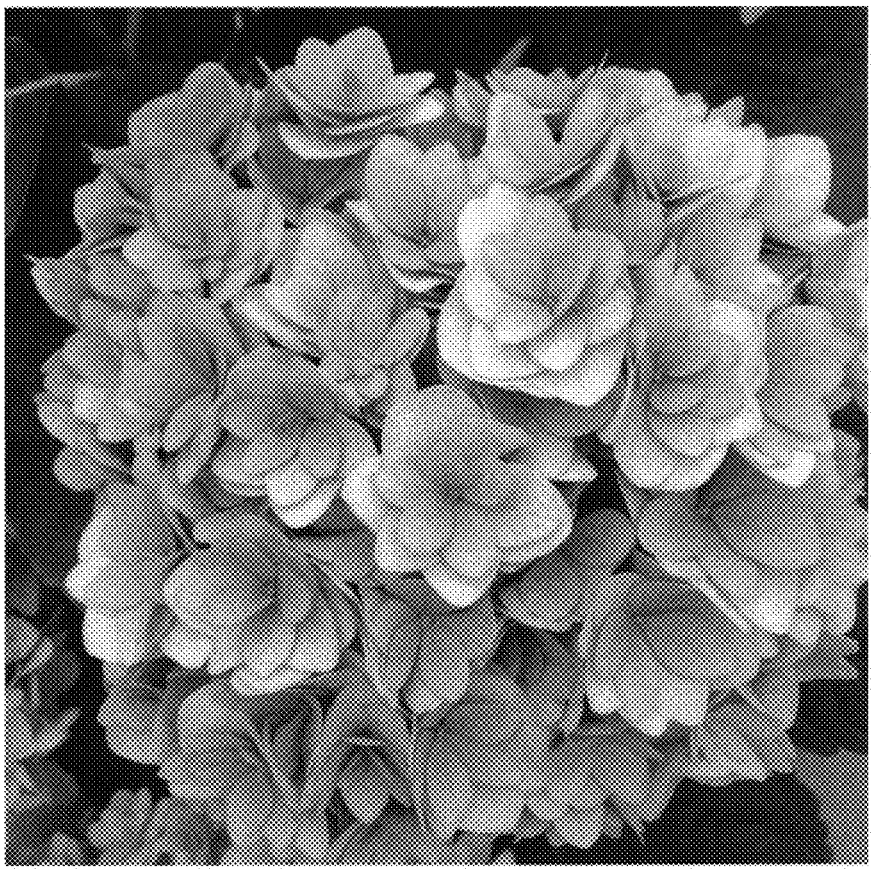

* * * * *